(12) United States Patent
Oyamada et al.

(10) Patent No.: US 6,565,356 B2
(45) Date of Patent: May 20, 2003

(54) DENTAL DIAMOND BUR

(75) Inventors: Yuuki Oyamada, Morioka (JP); Keisuke Ikushima, Tokyo (JP)

(73) Assignee: GC Corporation, Tokyo (JP)

( * ) Notice: Subject to any disclaimer, the term of this patent is extended or adjusted under 35 U.S.C. 154(b) by 86 days.

(21) Appl. No.: 09/962,536

(22) Filed: Sep. 26, 2001

(65) Prior Publication Data

US 2002/0037490 A1 Mar. 28, 2002

(30) Foreign Application Priority Data

Sep. 28, 2000 (JP) ........................................ 2000-296473

(51) Int. Cl.[7] ................................................. A61C 3/06
(52) U.S. Cl. ........................................ 433/166; 433/165
(58) Field of Search ................................ 433/165, 166; 451/540

(56) References Cited

U.S. PATENT DOCUMENTS

| | | | | |
|---|---|---|---|---|
| 2,807,264 A | * | 9/1957 | Tuck | 433/166 |
| 3,894,339 A | * | 7/1975 | Manzi | 433/166 |
| 4,190,958 A | * | 3/1980 | Martin et al. | 433/102 |
| 4,661,061 A | * | 4/1987 | Martin | 433/102 |
| 5,277,583 A | * | 1/1994 | Chalifoux | 433/220 |

* cited by examiner

*Primary Examiner*—John J. Wilson
(74) *Attorney, Agent, or Firm*—Oblon, Spivak, McClelland, Maier & Neustadt, P.C.

(57) ABSTRACT

A dental diamond bur is provided, which is applicable for operations including from opening of a pulp chamber to spreading of a root canal orifice to any teeth of anterior teeth and molars; does not cut out a tooth orifice portion more than needed; cuts out a tooth orifice surface into a smooth curve surface form, thereby improving the adhesion between a filler and a tooth in that cut-out site; and is free from occurrence of perforation, in the root canal treatment. The dental diamond bur includes a tip portion that is a body of revolution with a convergent smooth curve, having a diameter in a shank portion side thereof of 0.5 to 0.8 mm and a height of 0.5 to 0.85 mm; and a diamond grains-attached portion that is a body of revolution with an externally convex curve from a rear end of the front end portion toward a shank portion, a maximum diameter portion of the diamond grains-attached portion being positioned in a range of 5.0 to 10.0 mm from the tip of the front end portion, and the tip portion side of the diamond grains-attached portion constituting a smooth surface in which diamond grains are slightly protruded from the shank portion side of the tip portion.

2 Claims, 1 Drawing Sheet

DENTAL DIAMOND BUR

BACKGROUND OF THE INVENTION

1. Field of the Invention

The present invention relates to a dental diamond bur to be mounted in a dental handpiece, which is suitable for cutting safely and precisely a hard tissue of tooth, from which a tectorium portion thereof has been removed for the purposes of exposure and opening of an occlusal surface side of a pulp chamber filled with a dental pulp, within a short period of time, prior to a root canal treatment such as treatment of pulp removal, enlargement of a root canal, and filling medicine, in the dental remedy.

2. Description of the Conventional Art

In the dental root canal treatment, it is the most important to treat surely a root canal. In this root canal treatment, a dental cutting tool that is mounted in a dental handpiece to use, is used for not only cutting out of a tectorium portion of tooth and a horn of pulp chamber but also opening of a pulp chamber and spreading of a root canal, and is applied for a pretreatment of the enlargement of a root canal by a reamer or a file for the purposes of treatment of pulp removal by means of a cleanser, filling medicine, etc. to be carried out later. However, the shape of the pulp chamber or root canal is different between anterior teeth and molars. Further, it is also different among individuals. In addition, the pulp chamber or the interior of root canal becomes narrow by increased impaction of a secondary dentin by an increase in age. For these reasons, the shape of the pulp chamber or root canal is not in a definite form. Moreover, since the pulp chamber or root canal is positioned within a tooth, it is difficult to carry out the opening or enlargement under observation by naked eyes, and it is not easy to carry out the root canal treatment precisely within a short period of time.

Hitherto, as the dental cutting tool for root canal treatment, which is mounted in a dental handpiece and used for cutting out a tooth, have been employed burs having various forms such as a dental diamond bur in which diamond grains are electro-deposited on a stainless steel bar by plating, and a dental carbide bur in which a spiral blade or furrow is formed with tungsten carbide. However, in recent years, the dental diamond bur having good cutting properties, in which cut pieces are hardly scattered, has been widely used. With respect to the shape of the dental diamond bur for root canal treatment, are widely used a round-end bur having a spherical end and a hemispherical cone bur having a hemispherical cone-shaped end.

The root canal treatment using such dental diamond bur is carried out in the following procedures. That is, first of all, a dental caries portion and a tectorium portion are cut out and removed; the tectorium portion is completely removed from a lingual side in the case of anterior teeth and from an occlusal surface side in the case of molars, respectively, using a round-end bur or a hemispherical cone bur; and a horn of pulp chamber is subsequently removed, thereby making it easy to perform extirpation of pulp by a cleanser and enlargement of a root canal by a reamer or a file.

In this case, when the round-end bur having a spherical end is used, after perforating into the pulp chamber, the horn of pulp chamber is removed by scratching up by a shoulder of the round-end bur, thereby opening the pulp chamber. However, the aperture surface of tooth cut out by the round-end bur is liable to become in a rounded unevenness shape. As a result, when a filler is packed within the spread root canal later, the adhesion in a pulp cavity is possibly deteriorated. On the other hand, when the hemispherical cone bur is used, a transitional portion from the pulp chamber to the root canal does not become in a continuous flare shape, causing to form a difference in level. As a result, the operation by a reamer or a file to be effected later is liable to be adversely affected. Further, in the case of opening of pulp chamber, such as maxillary first molars, maxillary premolars, and mandibular anterior teeth, the teeth are often strongly flattened under pressure in a near centrifugal manner from the neighborhood of a cervix toward a root apex. As a result, in the vicinity of a root canal orifice, there is a danger that perforation occurs from a pulp chamber wall or a pulp chamber floor.

In recent years, for the purpose of preventing the perforation from occurrence, has been developed a dental diamond bur in a hemispherical cone shape, provided with a bare head portion where a ground surface ground of a stainless steel is exposed, without diamond grains being attached in a portion of about 1 to 3 mm from a tip thereof. In this dental diamond bur, since diamond grains are not attached to the tip thereof, the teeth are not cut out by the tip portion, and the perforation less possibly occurs even in the operation by an operator on a basis of the touch of fingers. However, since the currently commercially available dental diamond bur in a hemispherical cone shape having a bare head portion is in a tapered form in which the shape of the diamond grains-attached portion as a working portion becomes narrow at a constant rate toward the tip, a tooth surface cut out becomes also in a linear shape. In addition, in the case where the tectorium portion of tooth is cut out by a central portion or tip side of the dental diamond bur, a rear end portion of the dental diamond bur contacts with a tooth aperture portion and cuts it. As a result, the cutting-out amount of the tooth aperture portion becomes high more than necessary. Accordingly, with respect to the currently commercially available dental diamond bur, one that can be suitably used for the treatment including from the opening of a pulp chamber to the spreading of a root canal orifice is not present.

SUMMARY OF THE INVENTION

The present invention is aimed to provide a dental diamond bur, which is applicable for operations including from opening of a pulp chamber to spreading of a root canal orifice to any teeth of anterior teeth and molars; does not cut out a tooth aperture portion more than needed; cuts out a tooth aperture surface into a smooth curve surface form, thereby improving the adhesion between a filler and a tooth in that cut-out site; and is free from occurrence of perforation, in the root canal treatment.

In order to achieve the above-described aim, we, the present inventors made extensive and intensive investigations. As a result, it has been found that when a tip portion of the dental diamond bur is shaped in a body of revolution with a prescribed dimension, not having diamond grains attached thereto and having a convergent smooth curve form, not only perforation is prevented from occurrence, but also it is possible to carry out elimination of a tectorium portion and treatments including from opening of a pulp chamber to spreading of a root canal orifice, while bringing the tip portion into contact with a root canal orifice; and that when a diamond grains-attached portion of the dental diamond bur in a smooth curved continuous form, in which diamond grains are slightly protruded in a tip side thereof, is a body of revolution with an externally convex curve, and a maximum diameter portion thereof is arranged in a prescribed position apart from the tip portion, it is possible to prevent a tooth aperture portion from being cut out more than needed, and a cut-out surface of the tooth orifice portion can be made in a smooth curve surface form, leading to accomplishment of the present invention.

Specifically, the present invention is concerned with a dental diamond bur comprising a tip portion that is a body of revolution with a convergent smooth curve, having a diameter in a shank portion side thereof of 0.5 to 0.8 mm and a height of 0.5 to 0.85 mm; and a diamond grains-attached portion that is a body of revolution with an externally convex curve from a rear end of the tip portion toward a shank portion, a maximum diameter portion of the diamond grains-attached portion being positioned in a range of 5.0 to 10.0 mm from the front end of the tip portion, and the tip portion side of the diamond grains-attached portion constituting a smooth surface in which diamond grains are slightly protruded from the shank portion side of the tip portion. Further, it is preferred that the diamond grains-attached portion is a body of revolution with an externally convex curve having a length of 6 to 11.0 mm and a diameter in the shank portion side of 1.45 to 1.75 mm.

DESCRIPTION OF THE PREFERRED EMBODIMENTS

Figure 1:
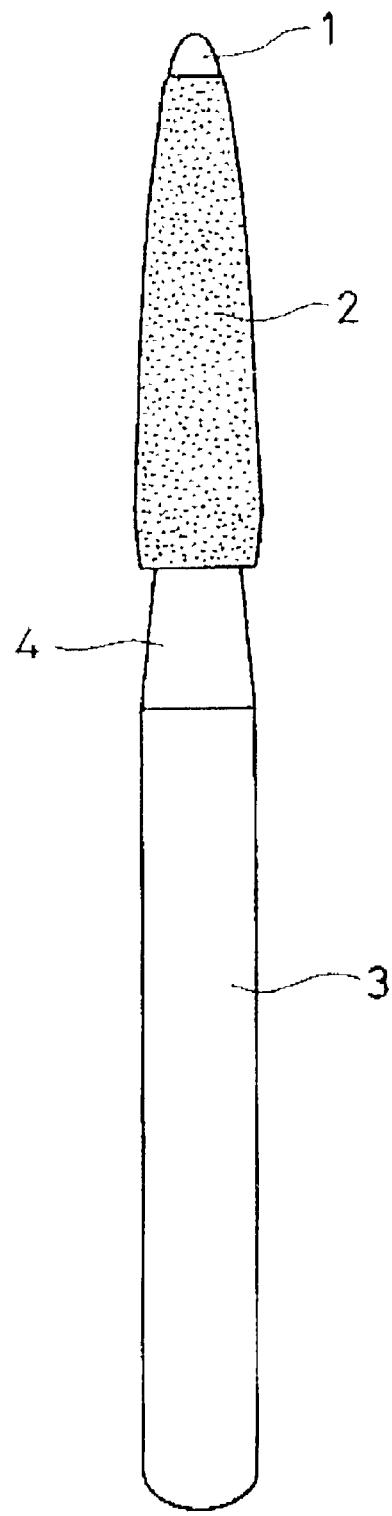
FIG. 1 is a front view of one embodiment of a dental diamond bur according to the present invention.

The dental diamond bur according to the present invention will be described in detail with reference to the accompanying drawing.

FIG. 1 is a front view of one embodiment of a dental diamond bur according to the present invention.

In the drawing, a numeral 1 is a tip portion in a shape of a body of revolution with a convergent smooth curve, having a diameter in the side of a shank portion 3 as described later of 0.5 to 0.8 mm and a height of 0.5 to 0.85 mm. Since diamond grains are not attached to this tip portion 1, the tip portion 1 forms a shape of a body of revolution in a smooth curve form and does not have cutting properties. Accordingly, even when opening of a pulp chamber or spreading of a root canal is carried out while bringing the tip portion 1 into contact with a pulp chamber floor, a root canal orifice, etc., it does not injure a pulp chamber wall, a pulp chamber floor, a root canal orifice, etc., and therefore, there is no danger to cause perforation. Further, since the tip portion 1 is in a shape of a body of revolution in a convergent smooth curve form, it is possible to find out the root canal orifice by the touch. The tip portion 1 is required to have a dimension such that a diameter in the side of the shank portion 3 is 0.5 to 0.8 mm and that a height is 0.5 to 0.85 mm. In the case where the diameter is smaller than 0.5 mm, the tip portion may possibly be inserted into a root canal depth. On the other hand, when it exceeds 0.8 mm, it is difficult to carry out spreading of a root canal of tooth having a thin root canal as in mandibular anterior teeth, and hence, such is not suitable. Further, when the height is shorter than 0.5 mm, in the case where the front end portion 1 is used in an inclined state, the pulp chamber floor or the pulp chamber wall is liable to be injured, so that it is difficult to use this tip portion 1 as a guide. On the other hand, in the case where the height is taller than 0.85 mm, it is impossible to cut out smoothly a transitional portion from the pulp chamber to the root canal, and hence, such is not suitable. Incidentally, in the embodiment as shown in FIG. 1, it is designed such that the diameter in the shank portion 3 side is 0.7 mm and that the height is 0.7 mm.

A numeral 2 is a diamond grains-attached portion constituting a continuous smooth surface in which the diamond grains in the side of the tip portion 1 are slightly protruded from the side of the shank portion 3 of the tip portion 1. The diamond grains-attached portion 2 is formed in a shape of a body of revolution with an externally convex curve from a rear end of the tip portion 1 toward the shank portion 3, and is formed in a flame-like shape having a maximum diameter portion of the diamond grains-attached portion 2 ranging from 5.0 to 10.0 mm. By making the side of the tip portion 1 convergent in such a way, not only it is easy to ensure a visual field, but also it is possible to improve the cutting efficiency by providing the maximum diameter portion in a portion having a high frequency in use. Further, by making the rear end in the side of the shank portion 3 thinner than the maximum diameter portion, not only the tooth orifice portion is prevented from being cut out more than needed, but also there is an effect for making the cut-out surface of the tooth orifice portion in a smooth curve surface form. The diamond grains-attached portion 2 is a portion in which diamond grains for cutting out a tooth are attached by electro-plating with Ni, etc., and in general, diamond grains having a grain size of about 75 to 110 μm are attached. Usually, since a thickness of the crown portion including an enamel and a dentin of a tooth is about 5 mm to 11 mm, a length of the diamond grains-attached potion 2 is preferably 6 to 11.0 mm. In the case where the length of the diamond grains-attached potion 2 is shorter than 6 mm, it is too short to cut out the dentin and the enamel during opening of the pulp chamber. As a result, it becomes necessary to carry out the cutting processing by moving the dental diamond bur according to the present invention up and down in a vertical direction, resulting in making the workability worse. On the other hand, in the case where it exceeds 11.0 mm, the length of the shank portion 3 becomes too short in the full length, so that a length for chucking into a turbine tends to be insufficient. Incidentally, it is necessary that the maximum diameter portion is positioned within a range of 5.0 to 10.0 mm from the front end of the tip portion 1. When the maximum diameter portion is positioned nearer than 5.0 mm toward the tip side, the tip side is too thick, so that not only it is impossible to ensure a visual field, but also the cutting efficiency in the tooth orifice portion is lowered. On the other hand, when the maximum diameter portion is positioned farther than 10.0 mm from the tip side toward the side of the shank portion 3, the resulting shape becomes similar to a hemispherical cone, whereby no effect by forming the shape in a flame-like form is found, and therefore, such is not suitable. Furthermore, it is preferred that the maximum diameter portion is positioned in a length portion of ¾ to $^{96}/_{100}$ from the side of the tip portion 1 of the diamond-attached portion 2. Incidentally, it is preferred that the maximum diameter portion has a thickness of less than 1.83 mm. When the thickness of the maximum diameter portion is 1.83 mm or more, the resulting shape becomes similar to a spherical shape, so that the operation tends to become difficult. Moreover, it is preferred that a diameter of the rear end in the side of the shank portion 3 of the diamond grains-attached portion 2 is 1.45 to 1.75 mm. When the diameter of the rear end in the side of the shank portion 3 is less than 1.45 mm, there is a danger that breakage occurs in a boundary between the shank portion 3 and the working portion during cutting because it is too thin. On the other hand, when it exceeds 1.75 mm, there may be generated a tendency that it is impossible to insert the diamond bur into a narrow side during cutting.

Incidentally, in the embodiment as shown in FIG. 1, it is designed that the diamond grains-attached portion 2 has a length of 7.1 mm, a diameter in the tip side of 0.74 mm, a diameter in the rear end side of 1.62 mm, a diameter of the maximum diameter portion of 1.68 mm, and a length from the front end of the tip portion 1 to the maximum diameter portion of 7.1 mm.

A numeral 3 is a shank portion that is chucked into a turbine and then held and rotated, and is formed in a round bar state, and has a rear end in a hemispherical shape. Due to the relationship with a dental turbine, it is defined according to the ISO standards that the thickness is 1.59 to 1.60 mm and that the length is 9 mm or longer. Incidentally, while the shank portion 3 may be continuous with the above-described diamond grains-attached portion 2, they may be connected through a neck portion 4 as in the embodiment shown in FIG. 1. This neck portion 4 may be either in a convergent form toward the side of the diamond grains-attached portion 2 as shown in FIG. 1, or in a clavate-like form. However, it is preferred that the thickness of the front end of the shank portion 3 is equal to or thinner than that of the rear end of the diamond grains-attached portion 2.

As described above, since the dental diamond bur according to the present invention is used in an oral cavity, it is preferred that the full length from the tip portion 1 to the rear end of the shank portion 3 is 19.5 to 25.0 mm. When the full length is shorter than 19.5 mm, in the case of long teeth having a length from the crown portion to the root apex portion of 23 to 26 mm, such as a maxillary first incisor and a canine tooth, there is a possibility that the dental diamond bur does not reach from the tooth orifice portion to the root canal. On the other hand, when the full length exceeds 25.0 mm, in the case where the dental diamond bur is used for the opening of a pulp chamber having a narrow space as in a second molar, a patient is forced to open largely his or her mouth, and hence, such is not preferred. Incidentally, in the embodiment as shown in FIG. 1, it is designed that the full length from the tip portion 1 to the rear end of the shank portion 3 is 22.0 mm.

As described above, in the case where the dental diamond bur according to the present invention is used in the root canal treatment, first of all, a dental caries portion and a tectorium portion are cut out and removed; the dental diamond bur according to the present invention, the shank portion 3 of which is set in a dental turbine, is inserted into a pulp chamber from a lingual side in the case of anterior teeth and from an occlusal surface side in the case of molars, respectively, thereby bringing the tip portion 1 into contact with a pulp chamber floor, a root canal orifice, etc.; and an enamel and a dentin of a tooth are cut out, thereby effecting the operations of enlargement of a pulp chamber or spreading of a root canal. In this case, since the tip portion 1 is formed in a shape of a body of revolution not having diamond grains attached thereto and having a convergent smooth curve form, the pulp chamber wall, the pulp chamber floor, the root canal orifice, etc. are not injured, and hence, no perforation occurs. Further, since the diamond grains-attached portion 2 is a body of revolution with an externally convex curve, and the maximum diameter portion of the diamond grains-attached portion 2 is arranged in a prescribed position apart from the tip portion 1, a cutting amount in the aperture portion of the tooth to be cut can be lowered to a minimum. Moreover, since the diamond grains in the side of the tip portion 1 of the diamond grains-attached portion 2 are slightly protruded from the side of the shank portion 3 of the tip portion 1, in the diamond grains-attached portion 2 the cutting can be carried out from the side of the tip portion 1 thereof, and the cut-out surface is formed in a smooth curve form. Thus, it is possible to effect a treatment for making it easy to carry out spreading of a root canal by a reamer or a file for the purposes of treatment of pulp removal by means of a cleanser, filling medicine, etc. to be carried out later.

As has been described above in detail, as a result of investigations on the form for carrying out the treatment including from the opening of a pulp chamber to the spreading of a root canal, the dental diamond bur according to the present invention is provided with a tip potion and a diamond grains-attached portion, as characterized above. Furthermore, the dental diamond bur according to the present invention overcomes the defects of the conventional hemispherical cone and enables one to effect a proper root canal treatment without any needs of a skill or a high technique. Moreover, the dental diamond bur according to the present invention can shorten a period of time when a patient opens his or her mouth and can lower the cutting amount in the orifice portion of the tooth to a minimum, and hence, can greatly reduce a pain to the patient. In the light of the above, the present invention is greatly valuable in contribution to the dental remedy.

While the invention has been described in detail and with reference to specific embodiments thereof, it will be apparent to one skilled in the art that various changes and modifications can be made therein without departing from the spirit and scope thereof.

What is claimed is:

1. A dental diamond bur comprising a tip portion that is a body of revolution with a convergent smooth curve, having a diameter in a shank portion side thereof of 0.5 to 0.8 mm and a height of 0.5 to 0.85 mm; and a diamond grains-attached portion that is a body of revolution with an externally convex curve from a rear end of the tip portion toward a shank portion, a maximum diameter portion of the diamond grains-attached portion being positioned in a range of 5.0 to 10.0 mm from the front end of the tip portion, and the tip portion side of the diamond grains-attached portion constituting a smooth surface in which diamond grains are slightly protruded from the shank portion side of the tip portion.

2. The dental diamond bur as claimed in claim 1, wherein the diamond grains-attached portion is a body of revolution with en externally convex curve having a length of 6 to 11.0 mm and a diameter in the shank portion side of 1.45 to 1.75 mm.

* * * * *